United States Patent [19]

Hansmann et al.

[11] Patent Number: 5,707,799
[45] Date of Patent: Jan. 13, 1998

[54] DEVICES AND METHODS UTILIZING ARRAYS OF STRUCTURES FOR ANALYTE CAPTURE

[75] Inventors: Douglas D. Hansmann, Libertyville; John P. Grace, Lake Villa; Michael G. Lowery, Wildwood; Gary M. Oosta, Gurnee, all of Ill.; Neil W. Loomis, Racine, Wis.; Eric B. Shain, Glencoe, Ill.; Thomas G. Schapira, Bristol, Wis.

[73] Assignee: Abbott Laboratories, Abbott Park, Ill.

[21] Appl. No.: 315,364

[22] Filed: Sep. 30, 1994

[51] Int. Cl.$^6$ .................. G01N 33/543; G01N 33/558
[52] U.S. Cl. .................. 435/6; 422/55; 422/57; 422/58; 422/101; 435/7.2; 435/7.9; 435/7.92; 435/7.93; 435/7.94; 435/7.5; 435/287.1; 435/287.2; 435/287.3; 435/288.2; 435/810; 436/164; 436/172; 436/804; 436/805; 436/809; 436/810
[58] Field of Search .................. 422/55, 56, 57, 422/58, 101; 435/6, 7.2, 7.9, 7.92, 7.93, 7.94, 7.5, 287.1, 287.2, 287.3, 288.2, 810; 436/514, 518, 527, 531, 164, 172, 804, 805, 809, 810

[56] References Cited

U.S. PATENT DOCUMENTS

| | | | |
|---|---|---|---|
| 4,789,628 | 12/1988 | Nayak | 435/7 |
| 5,304,487 | 4/1994 | Wilding et al. | 422/55 |
| 5,498,392 | 3/1996 | Wilding et al. | 422/55 |

FOREIGN PATENT DOCUMENTS

9322053  11/1993  WIPO .................. B01L 3/00

*Primary Examiner*—Christopher L. Chin
*Attorney, Agent, or Firm*—David L. Weinstein; Gregory W. Steele

[57] ABSTRACT

The present invention relates to analytical devices for determining the presence or amount of an analyte in a test sample. The analytical devices comprise an inlet port, a vent, a channel, and an array of structures. The structures have immobilized reagent covalently or non-covalently attached to the surface of the structures. The immobilized reagent captures analyte in the test sample where it is detected by a detection system. The present invention also provides methods and reagents for performing assays utilizing the analytical devices of the present invention. The present invention also provides methods of manufacturing the analytical devices of the present invention.

30 Claims, 2 Drawing Sheets

FIG. 6

DEVICES AND METHODS UTILIZING ARRAYS OF STRUCTURES FOR ANALYTE CAPTURE

FIELD OF THE INVENTION

This invention relates to analytical devices for the detection of analytes in a test sample. The devices utilize an array of structures in the device to capture the analyte.

BACKGROUND OF THE INVENTION

The qualitative or quantitative determination of analytes in test samples continues to be important in the diagnoses of physiological and non-physiological conditions. The analysis of a test sample mixed with reagents results in a detectable signal with and without the aid of instrumentation.

Methods and devices have been provided which give determinations of a variety of analytes in a test sample. Of particular interest for purposes of the present invention are small, disposable devices. Such devices generally involve either a strip or a track device.

Porous devices generally employ some form of porous material which carries a fluid through the device. These devices are generally in the form of sheets, strips, dipsticks, etc. Strip devices advantageously have a large surface area and small pores. One of the disadvantages of devices utilizing such materials is that the porous material can vary from lot to lot due to the random process in forming the devices. The variations can cause differences in the performance of the devices.

Track devices provide uniform surfaces which are readily reproducible yet provide too large a spacing to allow for diffusion of analyte and subsequent capture at an internal surface in a reasonable length of time.

Therefore, it would be advantageous to create small, disposable devices which have the dimensional reproducibility of track devices and the small pores and large surface area of devices employing porous material. The problems of porous devices and track devices would then be simultaneously solved.

Several processes have been used to create small devices in the electronic industry. For example, Munchmeyer et al., *Rev. Sci, Instrum.*, 63 (1) 713–721, (1992), discloses LIGA technology for producing optical and electrical microcomponents utilizing synchotron radiation lithography to produce masters. Angell et al., *Scientific American*, 248:44–55 (1983) teaches etching by micromachining technology into silicon wafers for microelectronics purposes. Manz et al., *Trends in Analytical Chemistry*, Vol. 10, No. 5, pp. 144–149, (1991), discloses reproducible micromachined monocrystalline silicon and glass for flow injection analysis and detector cells which provide for faster chromatographic and electrophoretic separations.

The trend to small devices is not limited to the electronics industry. Sato et al., *Sensors and Actuators*, A21–A23, pp. 948–953, (1990), discloses micromechanical silicon devices which permits one-to-one cell fusion operations between two different cell groups to be carried out simultaneously. Cells were found to fuse successfully in the microchambers.

U.S. Pat. No. 4,789,628 to Nayak discloses a plurality of spaced projections extending upward from the well bottom to provide increased surface area for ligand:anti-ligand assays. The plurality of spaced projections forms an interconnecting channel. However, the large sizes of the projections and large widths of the channels do not provide for microvolume assays or rapid signal development with low level analytes.

WO 93/22053 A1 to Wilding et al., discloses microfabricated detection devices which detect analyte in a test sample. The device has a micrometer scale channel extending from the inlet port. The channels were constructed by micromachining into silicon. Binding moieties line the channel which provides for analyte detection.

The current analytical techniques, namely porous and track devices, do not provide materials which result in satisfactory assay performance. There is a need for a reproducible device which permits microvolumes of fluid flow at acceptable rates and capture of analyte with acceptable efficiencies.

SUMMARY OF THE INVENTION

The present invention relates analytical devices for determining the presence or an amount of an analyte in a test sample comprising an array of structures wherein the structures have a surface providing a site for immobilizing reagent. The immobilized reagent is covalently or non-covalently attached to said surface of the structures and is capable of binding an analyte, analyte-analog, ancillary binding member, or a labelled reagent. The analytical devices of the present invention also comprise a plurality of channels wherein a test sample containing an analyte, analyte-analog, ancillary binding member, or labelled reagent can flows through the channels and the analyte, analyte-analog, ancillary binding member, or labelled reagent can diffuse across the width of said channels thereby binding to the immobilized reagent. The labelled reagent comprising a specific binding member conjugated to a detectable label wherein the detectable label produces a signal determining the presence or amount of the analyte present in the test sample.

The present invention also relates methods of utilizing the analytical devices of the present invention as well as methods of manufacturing such devices.

DETAILED DESCRIPTION OF THE INVENTION

Definitions

Before proceeding with the description of the various embodiments of the present invention, a number of terms used herein will be defined.

"Ancillary specific binding member" refers to any specific binding member which is used in the assay in addition to the specific binding members of the labelled reagent or immobilized reagent. One or more ancillary specific binding members can be used in an assay. For example, an ancillary specific binding member can be capable of binding the labelled reagent to the analyte of interest, in instances where the analyte itself could not directly attach to the labelled reagent. Alternatively, an ancillary specific binding member can be capable of binding the immobilized reagent to the analyte of interest, in instances where the analyte itself could not directly attach to the immobilized reagent. The ancillary specific binding member can be incorporated into the assay device, added to the sample, or added as a separate reagent.

"Analyte" or "analyte of interest" refers to the compound or composition to be detected or measured, which has at least one epitope or binding site. The analyte can be any substance for which there exists a naturally occurring analyte-specific binding member or for which an analyte-specific binding member can be prepared. Analytes include, but are not limited to toxins, organic compounds, proteins, lipids, fatty acids, peptides, microorganisms, amino acids, nucleic acids, hormones, sugars, steroids, vitamins, drugs (including those administered for therapeutic purposes as well as those administered for illicit purposes), and metabolites of or antibodies to any of the above substances. The term "analyte" also includes any antigenic substances, haptens, antibodies, macromolecules and combinations thereof.

"Analyte-analog" refers to a substance which cross-reacts with the analyte-specific binding member, although it may do so to a greater or a lesser extent than does the analyte itself. The analyte-analog can include a modified analyte as well as a fragmented or synthetic portion of the analyte molecule, so long as the analyte-analog has at least one epitopic site in common with the analyte of interest. An example of an analyte-analog is a synthetic peptide sequence which duplicates at least one epitope of the whole-molecule analyte so that the analyte-analog can bind to the analyte-specific binding member.

"Capillary", refers to a solid surface surrounding a void, in which air can be preferentially displaced by a liquid of the right surface tension. The mechanism for capillarity is dependent on the surface free energy of the system. For spontaneous spreading of the liquid to occur through a capillary, the surface free energy of the system must decrease during the spreading process. This can be accomplished for the devices used herein by selecting the appropriate solid surfaces for the biologic fluid of interest.

"Capture site" refers to a delimited or defined portion of the structures such that the specific binding reaction occurs between the immobilized reagent and the analyte.

"Chamber" refers to an enclosed space or cavity of defined dimensions that is not a capillary. The chamber may have inlet and outlet openings. The chamber can be filled by capillary forces or by differential pressure. The control of dimensions for a particular chamber allows for control of reagent additions, flow, incubation, reaction zones, or detection. In addition, reagent can be covalently or non-covalently attached to the surface of the chambers.

"Channels(s)," refers to the space between adjacent structures in the device. The channels can be also be capillaries. Generally, the channel has access to an inlet port, other capillaries, or a chamber. The channel length will be sufficient in length for analyte determinations and detections.

"Conjugation," refers to the chemical coupling of one moiety to another to form a conjugate. Coupling agents for covalent conjugation to protein have been described in U.S. Pat. No. 5,053,520, the entirety of which is hereby incorporated by reference. Homobifunctional coupling agents for coupling enzymes to antibodies are also known in the art as described in P.C.T. Publication Number WO 92/07268, published on Apr. 30, 1992.

"Coupling agent" refers to bifunctional crosslinking or coupling agents, i.e., molecules containing two reactive groups or "ends", which may be tethered by a spacer. The reactive ends can be any of a variety of functionalities including, but not limited to: amino reacting ends such as n-hydroxysuccinimide (NHS) active esters, imidoesters, aldehydes, epoxides, sulfonyl halides, isocyanate, isothiocyanate, and nitroaryl halides; and thiol reacting ends such as pyridyl disulfides, maleimides, thiophthalimides, and active halogens. Heterobifunctional crosslinking reagents have two different reactive ends, e.g., an amino-reactive end and a carboxyl-reactive end, while homobifunctional reagents have similar reactive moieties on each end.

Commercially available heterobifunctional reagents for use in the present invention include, but are not limited to, the maleimido-NHS active esters coupling agents such as m-maleimidobenzoyl-N-hydroxy-succinimide ester (MBS); succinimidyl 4-(N-maleimido-methyl)cyclohexane-1-carboxylate (SMCC); succinimidyl 4-(p-maleimidophenyl) butyrate (SMPB) and derivatives thereof, including sulfosuccinimidyl derivatives such as sulfosuccinimidyl-4-(N-maleimido-methyl) cyclohexane-1-carboxylate (sulfo-SMCC); m-maleimidobenzoyl-sulfosuccinimide 2.5 ester (sulfo-MBS) and sulfosuccinimidyl 4-(p-maleimidophenyl) butyrate (sulfo-SMPB).

Other heterobifunctional reagents include the commercially available active halogen-NHS active esters coupling agents such as N-succinimidyl bromoacetate and N-succinimidyl (4-iodoacetyl)aminobenzoate (SLAB) and the sulfosuccinimidyl derivatives such as sulfosuccinimidyl (4-iodoacetyl)aminobenzoate (sulfo-SIAB).

Another group of coupling agents is the heterobifunctional and thiol cleavable agents such as N-succinimidyl 3-(2-pyridylthio)propionate (SPDP). Thiol cleavable agents, such as N, N'-didansyl-L-cystine and L-cystine dimethyl-ester dihydrochloride, can also be used.

"Dead Zone(s)" refers to areas within the channel(s) where fluids accumulate or fluid flow is not in a forward direction from the inlet port to the detection area of the device.

"Diffusion" refers to the random motion of an entity due to collisions of surrounding fluid molecules. Diffusion results in a net movement of the entity from a higher to lower concentration levels of the entity.

"Immobilized reagent" refers to reagent that is covalently or non-covalently attached to the surface of the structure. The immobilized reagent can be applied to the surface of the structure by a variety of methods well known in the art, e.g., dipping, inscribing with a pen, dispensing through a capillary tube or through the use of reagent jet-printing or any other suitable dispensing techniques. The method of application and attachment are not critical to the present invention.

Generally, the immobilized reagent is a specific binding member that is attached covalently or non-covalently on a surface of the structure to form a "capture site". Typically, the immobilized reagent is selected to bind the analyte, the labelled reagent or a complex thereof. In preferred embodiments, the immobilized reagent binds to the analyte for the completion of a sandwich complex. The immobilized reagent may be chosen to directly bind the analyte or indirectly bind the analyte by means of an ancillary specific binding member which is bound to the analyte. The immobilized reagent may be immobilized on the structure before or during the performance of the assay by means of any suitable attachment method. In addition, the immobilized reagent can slow the migration of the analyte and/or labelled reagent through the channel. The immobilized reagent can be also attached to the structure in such a way that it can be removed by the fluid. In addition, the capture site can be marked, for example with a dye, such that the position of the capture site upon the structures can be visually or instrumentally determined even when there is no label immobilized at the capture site. Any dye can be utilized for this purpose as long as the dye does not interfere with the assay or components of the assay.

The immobilized reagent may be provided in a single capture site or in multiple capture sites. The immobilized reagent may also be configured to provide a variety of configurations i.e., to produce different detection or measurement formats. Alternatively, the immobilized reagent can be distributed over a large portion of the structure in a substantially uniform manner to form the capture site. The extent of signal production in the capture site is related to the amount of analyte in the test sample.

"Inlet port", or "entry port", or "sample in" are terms that are synonymous. They refer to the site where the test sample is introduced into the analytical device. The site accesses a receiving area of the device. The receiving area of the device can be a chamber, a capillary or a channel.

"Labelled reagent" refers to a substance comprising a detectable label attached to a specific binding member. The attachment may be covalent or non-covalent binding but the method of attachment is not critical to the present invention. The labelled reagent produces a detectable signal that is directly or indirectly related to the amount of analyte in the test sample. The specific binding member component of the labelled reagent is selected to directly bind to the analyte or to indirectly bind the analyte by means of an ancillary specific binding member, which is described in greater detail hereinafter. Additionally, the labelled reagent can comprise a detectable label attached to a specific binding member which specifically binds to the immobilized reagent. The labelled reagent can be incorporated into the test device, it can be combined with the test sample to form a test solution, it can be added to the device separately from the test sample or it can be predeposited or reversibly immobilized at the capture site. In addition, the specific binding member may be labelled before or during the performance of the assay by means of a suitable attachment method.

"Label" or "labelled" refers to any substance which is capable of producing a signal that is detectable by visual or instrumental means. Various labels suitable for use in the present invention include labels which produce signals through either chemical or physical means. Such labels can include enzymes and substrates; chromogens; catalysts; fluorescent compounds; chemiluminescent compounds; radioactive labels; direct visual labels including colloidal metallic particles such as gold, colloidal non-metallic particles such as selenium, dyed or colored particles such as a dyed plastic or a stained microorganism, colored or colorable organic polymer latex particles, and liposomes or other vesicles containing directly visible substances; and the like. Colloidal metals and dye particles are disclosed in U.S. Pat. Nos. 4,313,734 and 4,373,932. The preparation and use of non-metallic colloidals are disclosed in U.S. Pat. No. 4,954,452. Organic polymer latex particles for use as labels are disclosed in U.S. Pat. No. 4,252,459.

The selection of a particular label is not critical to the present invention, as long as the label is capable of generating a detectable signal either by itself, such as a visually detectable colored organic polymer latex particle, or instrumentally detectable, such as a fluorescent compound, or detectable in conjunction with one or more additional signal producing components, such as an enzyme/substrate signal producing system. A variety of different labelled reagents can be formed by varying either the label or the specific binding member component of the labelled reagent; it will be appreciated by one skilled in the art that the choice involves consideration of the analyte to be detected and the desired means of detection.

"Reaction mixture," as used herein, means a mixture of the test sample and other biological, chemical, and physical substances and reagents for the detection of analyte in the test sample. The reaction mixture can also include diluents and buffers.

"Signal producing component" refers to any substance capable of reacting with another assay reagent or with the analyte to produce a reaction product or signal that indicates the presence of the analyte and that is detectable by visual or instrumental means. "Signal production system", as used herein, refers to the group of assay reagents that are needed to produce the desired reaction product or signal. For example, one or more signal producing components can be reacted with the label to generate a detectable signal, e.g., when the label is an enzyme, amplification of the detectable signal is obtained by reacting the enzyme with one or more substrates or additional enzymes and substrates to produce a detectable reaction product.

"Specific binding member" refers to a member that specifically binds to another molecule through chemical or physical means. In addition to antigen and antibody specific binding members, other specific binding members include, as examples without limitation, biotin and avidin, carbohydrates and lectins, complementary nucleotide sequences, complementary peptide sequences, effector and receptor molecules, enzyme cofactors and enzymes, enzyme inhibitors and enzymes, a peptide sequence and an antibody specific for the sequence or the entire protein, polymeric acids and bases, dyes and protein binders, peptides and specific protein binders (e.g., ribonuclease, S-peptide and ribonuclease S-protein), and the like. Furthermore, specific binding members can include molecules that are analogs of the original specific binding member, for example an analyte-analog or a specific binding member made by recombinant techniques or molecular engineering. If the specific binding member is an immunoreactant it can be, for example, an antibody, antigen, hapten, or complex thereof, and if an antibody is used, it can be a monoclonal or polyclonal antibody, a recombinant protein or antibody, a chimeric antibody, a mixture(s) or fragment(s) thereof, as well as a mixture of an antibody and other specific binding members. The details of the preparation of such antibodies and their suitability for use as specific binding members are well-known to those skilled in the art.

"Structures" refers to the physical form that arises from the base layer of the devices of the present invention. The surfaces of the structures provide a large surface area. The structures are arranged in a pattern or array to provide sufficient analyte capture at capture sites on the surfaces of the structures. A variety of shapes can be used for the structures. For example, triangular structures can be utilized for capturing analyte. In addition, several different shapes can be used together in the same device, e.g., triangular structures and diamond shaped structures can be used in the same device to capture reagent.

"Test sample," refers to the sample containing an analyte to be detected using the present invention. A test sample can contain other components besides the analyte, can have the physical attributes of liquids, biological liquids, or a solid wherein the solid can be made soluble in a liquid, and can be of any size or volume, including for example, a moving stream of liquid. The test sample can contain any substances other than the analyte as long as the other substances do not interfere with the analyte or the analyte-analog. Examples of test samples include, but are not limited to: serum, plasma, foods, spinal fluid, sputum, seminal fluid, amniotic fluid, urine, saliva, other body fluids, and environmental samples such as ground water or waste water, soil extracts and pesticide residues.

DESCRIPTION OF THE INVENTION

The devices of the present invention utilize an array of structures for capturing analyte in a test sample. The structures are arranged in an array to provide essentially uniform channels for fluid transport and a large surface area. The analyte diffuses in the test sample where it is captured by a specific binding member bound on the surface of the structures. The analytical devices of the present invention can be utilized as sheets, dipsticks, strips, cuvettes, etc. In addition, the presence or amount of more than one analyte can be determined in a single analytical device. The present invention preferably provides devices and methods, where the devices rely on capillary action or differential pressure to drive movement of fluids through the device in order to control measurement of fluids, staging of events, capture of reagents or entities, reaction times, mixing of reagents, and to determine a detectable signal, etc. By varying the path through which the fluid flows, one can provide for a variety of activities such as mixing, incubating, reacting and detecting.

1. Methods of Manufacturing the Devices of the Present Invention

The analytical devices of the present invention rely on an array of structures in the device for analyte capture. The structures can be made by a variety of processes including, but not limited to lasering, embossing, Lithographie Galvanoformung Abformung (LIGA), electroplating, electroforming, photolithography, reactive ion etching, ion beam milling, compression molding, casting, reaction injection molding, injection molding, and micromachining the material. As will be understood, the methods utilized to manufacture the structures of the present invention are not critical as long as the method results in large quantities of uniform structures and devices. Furthermore, the method must result in a large surface area of the structure and arranged in close proximity to each other to produce narrow channels. The narrow channels allow analyte diffusion in the fluid to occur to enhance the efficiency of capturing analyte and/or labelled reagent at the capture site. Generally and preferably, the structures in the analytical device are made of the same material as the base layer of the device.

All of these techniques start with a technology which will produce a master. A tool is usually made from the master which will then be used to mass produce the analytical devices of the present invention, or, in some cases, the masters can be made in sufficient quantity to be used directly as the analytical devices of the present invention.

The mass produced structures are preferably made of any number of polymeric materials. Included among these are, but not intended to be limited to, polyolefins such as polypropylene and polyethylene, polyesters such as polyethylene terephthalate, styrene containing polymers such as polystyrene, styreneacrylonitrile, and acrylonitrilebutadienestyrene, polycarbonate, acrylic polymers such as polymethylmethacrylate and poly acrylonitrile, chlorine containing polymers such as polyvinylchloride and polyvinylidenechloride, acetal homopolymers and copolymers, cellulosics and their esters, cellulose nitrate, fluorine containing polymers such as polyvinylidenefluoride, polytetrafluoroethylene, polyamides, polyimides, polyetheretherketone, sulfur containing polymers such as polyphenylenesulfide and polyethersulfone, polyurethanes, silicon containing polymers such as polydimethylsiloxane. In addition, the structures can be made from copolymers, blends and/or laminates of the above materials, metal foils such as aluminum foil, metallized films and metals deposited on the above materials, as well as glass and ceramic materials.

In one such method, a laser, such as an excimer laser can be used to illuminate a photomask so that the light that passes through the photomask ablates an underlying material forming channels in the material substrate. Sercel, J., et al., SPIE Proceedings, Vol. 998, (September, 1988). This technique can be used to make a master. The master can directly be used as a device and produced in large quantities or can be used as a template to fabricate a tool which will be used to reproduce devices in large quantities.

Another method to make the devices is the LIGA technique, described by D. Munchmeyer et al., Rev. Sci. Instrum., 63 (1), 1992. An X-ray synchrotron source is used to irradiate a photoresist. The developed photoresist forms a master which can be electroplated with nickel to form a mold cavity. A liquid polymer can then be cast or injected into the nickel mold. This technique can be used to directly make analytical devices or to fabricate a tool from a master.

Another method to make the devices of the present invention is to use semiconductor manufacturing techniques such as, but not intended to be limited to, photolithography, reactive ion etching, and ion beam milling to define appropriate structures in photoresists or other materials. These techniques can be used to make devices directly or can be used to make a tool from which large quantities of devices can be made.

Still yet another method to make the devices of the present invention is to micromachine them. Micromachining involves the process of utilizing fine tools to cut channels into materials such as, but not limited to, steel, plastic, synthetic and non-synthetic polymers, silicon wafers, and other metals, ceramics and glass. These techniques can be used to make devices directly or can be used to make a tool from which large quantities of devices can be made.

Tools which are fabricated to mass produce the analytical devices of the present invention can be made from the above techniques. The tools can be made by a means such as, but not intended to be limited to, electroplating. This process generates a hardened tool, such as nickel, for reproducing the master.

Once a tool has been fabricated, analytical devices can be mass produced by, but not intended to be limited to, embossing, injection molding, reaction injection molding, casting, and compression molding. Embossing involves impressing a heated durable tool into a heated polymer substrate. Alternatively, a cool tool can be impressed into a heated polymer substrate. Injection molding uses a molten polymer to be injected into a mold cavity. Reaction injection molding injects a liquid resin which solidifies by a chemical process. Casting uses a low pressure molding process.

Compression molding utilizes a heated tool which melts and shapes the devices.

2. Configuration of the Devices of the Present Invention

Generally, the devices of the present invention will comprise an inlet port to which the test sample is initially presented. Generally, the channels are capillaries and provide transport of the test sample from the inlet port through the device, an array of structures which provide a capture site, and a vent, such as an exit port, which vents gases in the device. In addition, chambers and additional capillaries may be added to customize a device. Generally, test sample movement through the device relies on capillary forces. In addition, one or more capillaries can be used to bring the test sample from the inlet port to the channels. Additionally, one or more capillaries can be used to exit the structures area of the device. However, differential pressure may be used to drive fluid flow in the devices in lieu of, or in addition to capillary forces.

In lieu of an exit port, self-venting materials may be used to vent gases in the device as well as provide for oxygen intake into the device. The oxygen can be used in reactions, e.g., oxidase reactions, within the device. Self-venting materials and their uses in analytical devices are taught in U.S. patent application Ser. No. 08/174,973 filed Dec. 29, 1993 and copending U.S. patent application Ser. No. 08/229,256 filed Apr. 18, 1994, and are both hereby incorporated by reference.

Figure 1:
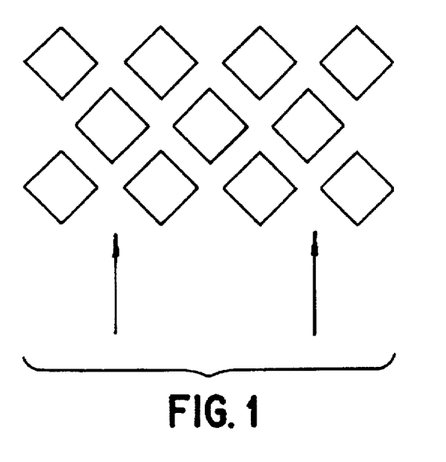
FIG. 1 depicts an array of diamond shaped structures. The surfaces of the structures are the capture site for analyte. The arrows in the figures represent the direction of fluid flow in the device. The rows of diamonds in the array are staggered relative to the direction of fluid flow.
Figure 2:
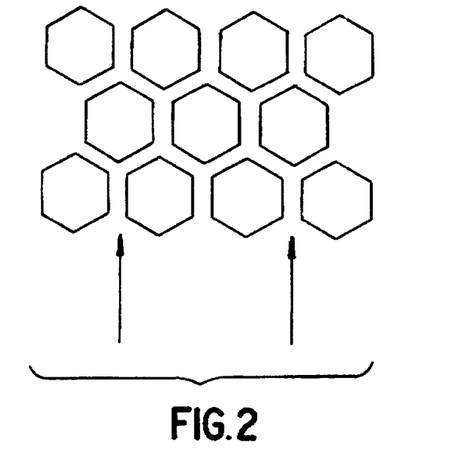
FIG. 2 depicts an array of hexagonal shaped structures to be used in the analytical devices of the present invention.
Figure 3:
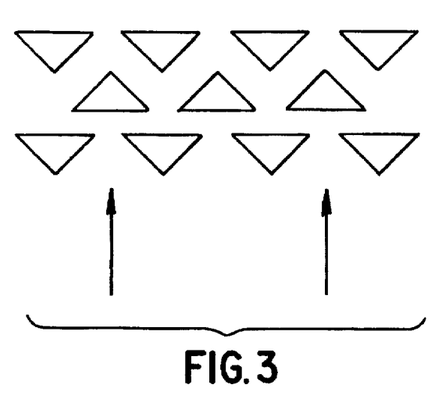
FIG. 3 depicts an array of triangular shaped structures to be used in the analytical devices of the present invention.
Figure 4:
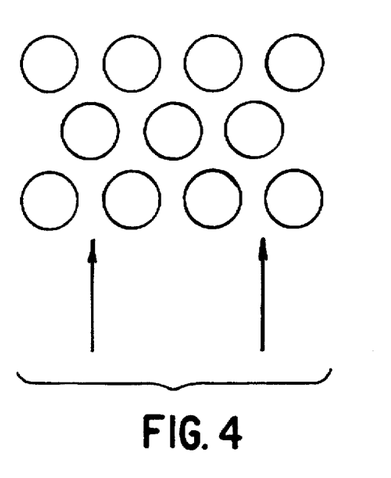
FIG. 4 depicts an array of circular shaped structures to be used in the analytical devices of the present invention.
Figure 5:
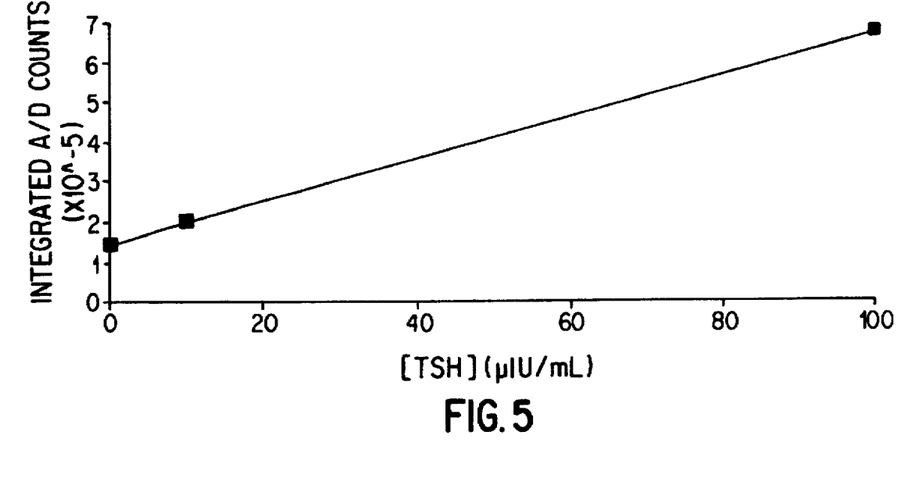
FIG. 5 shows the results of a hTSH assay as performed in Example 1 utilizing an analytical device of the present invention.
Figure 6:
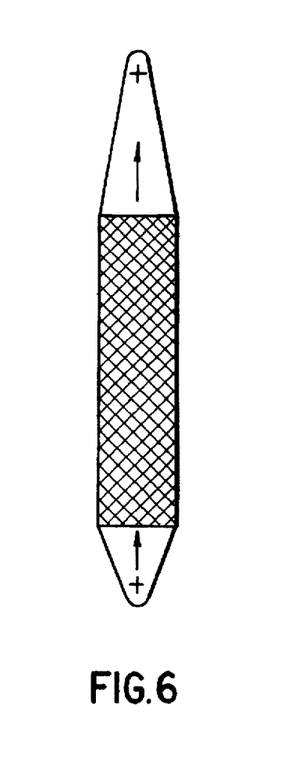
FIG. 6 depicts an embodiment of an analytical device of the present invention.

Channels are created between adjacent structures through which fluid can flow. Both the channel and structure designs are important to optimize contact between the structure surfaces and fluid molecules. Typically, the depth of the channels range from about 1 micrometer (µm) to about 1 millimeter (mm). The average width of the channels typically range from about 0.02 µm to 20 µm. The structures height ranges typically from about 1 µm to 1 mm and the average width typically ranges from 1 µm to 1 mm. Any number of configured arrays of structures can be selected so long as the dead zones are minimized or eliminated. The preferred configurations of the array of structures are arranged in an array, such as an array of diamonds, an array of octagons, an array of hexagonals, or the like. The preferred structures minimize dead zones. FIGS. 1,2, 3, and 4 show the preferred configurations of the structures. In addition, more than one area of structures can be arranged in a series. The series of arrays can be connected to each other by a capillaries.

Assays performed in the devices of the present invention optimize capture at the surface of the structure. By utilizing the methods taught herein, tight control of the capture site geometry improves the uniformity and efficiency of capture. The narrow, deep channels and the large surface area of the structures provides for diffusion of analyte and enhanced analyte capture. The channel design is based on diffusion of an entity in the test sample to interact with immobilized reagent on the surface of the structures. Typically, the entity is randomly distributed in the cross section of the channel. The entity diffuses to the structure surface where the entity can interact with immobilized reagent.

Immobilized reagent can be covalently or non-covalently attached onto the surface of the structures as well as within the capillaries and/or chambers. The reagent can be applied as a time-released reagent, spatially separated reagent, or coated and dried onto the surface. Such techniques of placing immobilized reagent on the surfaces are well known to those skilled in the art.

The methods for utilizing devices of the present invention involve specific binding members The methods of detection may involve the binding of a colored label such as a fluorescent dye or a colored particle. Alternatively, detection may involve binding of an enzyme which can produce a colored product.

Since the devices rely upon capillaries or other chambers to control movement of fluids, accurate control of dimensions of the internal chambers is essential. The devices of the present invention can be utilized in agglutination, competitive, non-competitive and sandwich assays as well as with standard clinical chemistry assays such as for glucose and cholesterol. Assays can be homogeneous where a separation means is not necessary or heterogeneous where a separation step is utilized. Typically, assays performed in the devices of the present invention are homogeneous.

One or more alternate flow paths can be used in the devices of the present invention. The capillary transporting the test sample from the inlet port branches in different pathways, the main pathway to the structures and the alternate pathways. The alternate pathways can reenter the main pathway at some distance from the branching point. If the fluidic resistance of the alternate pathway is approximately the same as the main pathway, the flow of test sample will proceed equally through the pathways of the device. If the alternate pathway has a fluidic resistance that is substantially greater than that of the main pathway, the flow in the alternate pathway will be slower. If the alternate pathway has a fluidic resistance less than the main pathway, the flow of the test sample in the alternate pathway will be greater. The fluidic resistance can be varied within each patway by varying the cross-sectional area of the flow, surface tension, venting, and viscosity of the test sample. These parameters and the distance can determine the time for reentry to the main pathway. Alternatively, each alternate pathway can flow directly to their own separate array of structures at indepedent flow rates. This would allow for multiple capture sites and allow simultaneous determinations of the presence or amount of multiple analytes in a single test site.

The alternate pathways can include areas for mixing of reagents with test samples. For example, chambers can be used as areas of reagent addition. The chamber or chambers can be placed in the alternate pathway as well as the main pathway.

In addition, trapping devices may be included in the device pathway so as to remove fluid constituents above a certain size. For example, the devices of the present invention can include separators, e.g., to separate plasma or serum from whole blood. For example, a matrix of hydrophilic sintered porous material can have a red blood cell agglutinating agent applied to its surface. The matrix could be placed in the device anterior to the structures. The red blood cells in the whole blood sample become entrapped in the interstices of the matrix while substantially blood cell free serum or plasma passes through the matrix and is transported by capillary action to the structures part of the device. U.S. Pat. No. 4,933,092 is hereby completely incorporated by reference.

An advantage of the devices of the present invention is that it allows microvolumes of test samples to be tested for the presence or amount of an analyte. For example, microvolumes of serum or plasma from a whole blood sample can be used to test for analyte.

Test samples containing an analyte to be detected may be a fluid which is used directly as obtained from the source or may be pretreated in a variety of ways so as to modify its character. The test sample will then be introduced into the device through an inlet port which accesses a receiving area of the device. The receiving area of the device will be either a chamber or a capillary. The test sample will then transported via the capillary. The test sample can encounter one or more reagents within the capillaries, the chambers anterior to the structures, or on the surfaces of the structures. The reagents may involve a system from which a detectable signal can be produced.

Any liquid test sample may be employed, where the test sample will have a reasonable rate of flow due to the capillary action or differential pressure. It is to be understood that the capillary action or differential pressure is the driving force of test sample transport. Capillary action depends on three critical factors; (1) the surface energies of the gas, surface on which the fluid flows, and fluid, (2) the dimensions of the capillary channel, and (3) the efficiency of venting. The flow rate for both capillary flow and differential pressure flow will be influenced by the geometry of the capillary or chamber and the viscosity of the fluid. The flow rate can be further impacted by increasing or decreasing the differential pressure. Methods of applying differential pressures include, but are not intended to be limited to, manual, motors, pumps, vacuums or the like.

If the test sample is too viscous, it can be diluted to provide for a capillary flow rate which allows for a reasonable flow time which will control the time period for the assay.

The test sample may be derived from a source such as, but is not intended to be limited to, a physiological fluid such as blood, serum, plasma, saliva, ocular lens fluid, cerebral spinal fluid, pus, sweat, exudate, urine, milk or the like. The test sample may be subject to prior treatment such as, but not intended to be limited to, extraction, addition, separation, dilution, concentration, filtration, distillation, dialysis or the like. Besides physiological fluids, other liquid test samples may be employed and the components of interest may be either liquids or solids whereby the solids are dissolved or suspended in a liquid medium.

The test sample medium employed may be naturally occurring medium or the test sample can be introduced into a liquid medium which provides the desired characteristics necessary for capillary action and a detectable signal. Additives and solvents can be added to the test sample medium to increase or decrease oxygenation, stability and fluidity.

Methods of detection include, but are not intended to be limited to, changes in color, light absorption, or light transmission, pH, conductivity, fluorescence, change in physical phase or the like.

Test samples may provide a detectable component of the detection system, or such components may be added. The components will vary widely depending on the nature of the detection system. One such detection method will involve the use of particles, where particles provide for light scatter or a change in the rate of flow. Particles may be, but are not intended to be limited to, cells, polymeric particles which are immiscible with a liquid system, latex particles, charcoal particles, metal particles, polysaccharides or protein particles, ceramic particles, nucleic acid particles, agglutinated particles or the like. The choice of particles will depend on the method of detection, the dispersability or the stability of the dispersion, inertness, participation in the change of flow, or the like.

The binding of an analyte to a specific binding member at the capture site can be optionally detected by monitoring the pressure of the test sample in the device. For example, a pressure detector connected to the test sample entering and exiting the channel will allow the detection of pressure decreases caused by analyte binding which results in channel flow restriction.

Another method of detection includes hybridization assays. The surface of the structures can be coated with an immobilized reagent such as polynucleotide probes. Upon binding of the complementary analyte polynucleotide to the immobilized polynucleotide probe, a labelled probe, e.g., a fluorescent-labelled probe can be added to bind to the analyte polynucleotide. The amount of fluorescence is directly proportional to the amount of analyte in the test sample. Alternatively, the hybridization assay can be performed in a competitive format where a polynucleotide is conjugated to a detectable label. The polynucleotide labelled reagent competes with the analyte for binding to the immobilized polynucleotide.

The reaction of an analyte with a specific binding member at the capture site may be detected by means of agglutination. For example, a fluorescent or luminescent labelled molecule capable of binding to the analyte or the analyte/specific binding member complex at the capture site may be used to detect for the presence or amount of analyte in the test sample. For example, the agglutination of blood cells at the capture site can serve as a positive test for the blood type of the test sample. The immobilized reagent on the surface of the structures induces agglutination thereby giving a positive test for blood type.

Luminescence may be detected in devices of the present invention. For example, luminescence emission may be readily detectable using a microplate reader. The analyte may be detected by a specific binding member comprising two antibodies capable of binding to the analyte, wherein one antibody is labelled with fluorescein, which emits light, and a second antibody is labelled with rhodamine, which absorbs light. When the rhodamine and fluorescein label antibodies each bind to the analyte, a quenching of the fluorescein can be observed, indicating the presence of the analyte. Another example is where the fluorescein antibodies immobilize at the capture site. The analyte and the rhodamine labelled antibody are then delivered to the capture site and quenching of the fluorescein is observed indicating the presence of the analyte.

Yet another detection system can include chemical detection. For example, glucose measurement correlates changes in absorption or reflectance of the medium with glucose concentration. One common method for glucose determination employs glucose oxidase (GOD) and peroxidase (POD) along with 4-aminoantipyrene (4-AAP) and dichlorohydroxybenzene sulfonate (DCHBS) to measure glucose levels in urine or serum. All reagents are combined into a water swellable matrix such as gelatin, and disposed over the structures. The structures are top laminated with a clear film such as polyethylene terephthalate (PET). The test sample, usually serum or urine, is introduced into the inlet port. Upon contact with the test sample, the gelatin disposed on the structures swells and releases the reagents which react with glucose. On reaction with glucose a soluble red dye is formed which can be measured by absorbance, reflectance or by visual observation.

Alternatively, POD or GOD can be immobilized on the structures and 4-AAP and DCHBS can be introduced with the test sample, initiating the reaction.

Sometimes, it is convenient to immobilize the color forming reagents in an assay for glucose, cholesterol or similar analytes. In this case, ballast groups, long chain alkyl groups, can be added to one part of the dye molecule to render it less soluble. Examples of dye molecules rendered less soluble by the incorporation of a ballast groups can be found in the Principles and Chemistry of Color Photography, Thirtle, J. R. in The Theory of the Photographic Process, 4th Edition., T. H. James, Ed., MacMillian Publishing Co., Inc., New York., 1977, pp. 369–372, hereby incorporated by reference. Ballasted DCHBS analogs could be coated directly onto the structures allowing color formation to occur only in one localized area of the structures.

Detection can also be done utilizing enzymes. The immobilized reagent specifically bind to the analyte. The labelled reagent comprises an enzyme conjugated to a specific binding member to the analyte. A substrate for the enzyme is added thereby causing an enzymatic reaction between the enzyme and the substrate. The amount of the enzyme detected and measured can be correlated to the amount of analyte present in the test sample. For example, alkaline phosphatase is commonly used as an enzymatic detection reagent in diagnostic assays, particularly specific binding assay formats. Alternatively, the labelled reagent can comprise an enzyme and a specific binding member that specifically binds to the immobilized reagent. A substrate for the enzyme is added thereby causing an enzymatic reaction between the enzyme and the substrate. The amount of the enzyme detected and measured can be correlated to the amount of analyte present in the test sample.

The analytes of interest are widely varied depending upon the purposes of the assay and the source of the test sample. Analytes may include a protein, a peptide, an amino acid, a carbohydrate, a hormone, asteroid, a vitamin, a lipid, a nucleic acid, a trace element, a drug including those administered for therapeutic purposes as well as those administered for illicit purposes, a bacterium, a virus, and a metabolite. Aggregation of molecules may also be of interest, particularly naturally occurring aggregations such as viroids, viruses, prokaryotic and eukaryotic cells including unicellular microorganisms, mammalian cells such as lymphocytes, epithelial cells, neoplastic and the like. Additionally, analytes can be any substance for which there exists a naturally occurring binding molecule (e.g., an antibody binding receptor) or for which a binding molecule can be prepared, and the analyte can bind to one or more binding molecules in an assay. Analyte thus includes antigenic substances, haptens, antibodies, combinations thereof, and the like.

Other additives may be included for specific purposes. Buffers may be desirable to maintain a particular pH. Enzyme inhibitors may be included as well. Other reagents of interest are, but are not intended to be limited to, antibodies, enzymes, antigens, peptides, biotin/avidin, preservatives, stabilizers, activators, enzyme substrates and cofactors, oxidants, reductants, or the like. As will be understood, the additional additives or reagents shall not interfere with assay performance.

In addition, a control means can be used to verify an assay result. One control means comprises a confirmatory assay that is performed essentially automatically and simultaneously with the assay for the detection of analyte. In a particular embodiment, the test sample containing the analyte is contacted with a predetermined amount of labeled reagent to form a mixture containing an analyte/labelled reagent complex. The resulting mixture is transported through the device by capillary action. In a first pathway, the mixture contacts a capture site containing an immobilized anti-analyte specific binding member that binds the analyte/labelled reagent complex. This capture site is the test sample capture site. In a second pathway, the mixture first contacts a reagent zone containing a positive control reagent. The positive control reagent is a mobile specific binding member having the same binding specificity for the labeled reagent as the test sample analyte. The positive control reagent can be either an analyte identical to that of the test sample or a corresponding analyte-analog. When the mixture contacts the positive control reagent zone, the positive control reagent is reconstituted and binds specifically with unbound labeled reagent to form a positive control reagent/labelled reagent complex. This complex migrates to the positive control capture site. The positive control capture site contains the same immobilized anti-analyte specific binding member as the first pathway. Therefore, the positive control capture site is capable of forming a detectable immobilized complex. A detectable signal at the positive control capture site confirms that the assay reagents are functional and the test result valid. For example, when no analyte is present in a test sample, the negative result of the test sample is confirmed as a valid test result when the positive control capture site has a detectable signal and the test sample site has no detectable signal. When analyte is present in a test sample, the positive result of the patient sample is confirmed as a valid test result when the positive control capture site has a detectable signal and the test sample capture site has detectable signal. No detectable signal at the positive control capture site itself, indicates either that the labelling system's reagents have degraded or that other factors in the test sample have interfered with the binding of the labelled reagent to the positive control reagent or with the binding of the labelled positive control complex to the immobilized specific binding member located at the positive control capture site.

The devices of the present invention may also incorporate additional control mechanisms and/or areas, e.g., to indicate the end of an assay. These other control mechanisms are well known to those skilled in the art.

The device can have various regions that can be used for reagent addition, filtration and the like as well as having separate areas where capillary action and differential pressure separately drive the fluid flow.

The types of assays utilizing the analytical devices of the present invention are numerous. In sandwich assays, the labelled reagent which comprises a specific binding member with affinity to the antigen is allowed to bind the immobilized specific binding member/analyte complex. The signal response is directly proportional to the analyte concentration.

In competition assays, competition is established between the analytes and the labelled reagent. The signal response is inversely proportional to the analyte concentration.

The devices of the present invention can also be made in the form of a cuvette. The structures can be made inside a housing which has a transparent window which will allow instruments to detect capture at the capture site. The cuvette can be placed in a spectrophotometer and read. For example, a cuvette can be constructed by placing a top layer of Pilcher Hamilton Film (Pilcher Hamilton Corporation, Greer, S.C., 29651) on top of the device of the present invention. An inlet port can be placed in the top layer or can remain as a part of the device. A double stick adhesive tape (3M Corp., St. Paul, Minn., 55144) was applied to the under surface of the top layer. A test sample can be placed into the inlet port and capture occurs at the capture sites.

The devices of the present invention can also be made in the form of an assay strip wherein one end of the assay strip is brought into contact with a liquid test sample containing an analyte. The test sample is transported through the device by capillary action where capture of analyte will occur at the structures. Such devices can also be made in the form of dipsticks. U.S. Pat. No. 5,200,317 is hereby completely incorporated by reference.

The devices of the present invention can also test multiple analytes in a single analytical device. Different and/or separate regions of structures can be designed, each having an immobilized reagent specific for a different analyte placed on them which will bind the respective analyte and/or labelled reagent. The separate regions of structures can be arranged in a series or can be arranged with multiple pathways. Instrumentation can be programmed to read the different regions independently. One such example is a drugs of abuse assay whereby one region of the structures has anti-benzoylecognine antibodies immobilized on it, another region of the structures has immobilized anti-cannabinoid antibodies, and another region of the structures has immobilized anti-amphetamine antibodies. A test sample containing metabolites and/or molecules of any or all of the three drugs will bind to their respective regions. Detections of positives and negatives can be done visually and/or with instrumentation. Each region of the structures testing for a different analyte can have specific reagents immobilized for that analyte.

3. Channel Design for Capture of Entities By Diffusion

The following is a summary of equations needed to approximate capture efficiency in devices of the present invention which use structures for analyte capture. The equations have been generalized for application to an arbitrary cross-sectional geometry of the channels. These equations should address a wide variety of potential channel designs. Since the equations apply to a general design, they do not directly provide a numerical prediction of capture efficiency. Instead, the channel cross-sectional shape must first be defined and the corresponding fluid velocity distribution, $U(y,z)$, must be precalculated using standard methods. Then, by incorporating these two values into the equations, a unique numerical approximation of capture efficiency can be derived and correlated versus such parameters as channel length (L), entity diameter (d), and wall reaction coefficients (k). Two example channel cross-sections for which a numerical result can readily be formulated include a rectangular and a circular shape. There are, however, no limits regarding the type of cross-sectional shape which can be evaluated.

All analytical assumptions implied by the equations are described below. These define the range of channel designs and flow conditions for which the equations are valid.

Primary Assumptions for Calculations

1. Steady-state fluid conditions. The fluid (with entities) completely fills the channel, and fluid velocity does not vary with time.
2. Laminar, incompressible flow. This assumption is applicable to all liquid types and flow rate values discussed.
3. Dilute entity concentration levels (less than 5% by volume). This ensures that the fluid velocity distribution can be solved independently of entity presence, and that no appreciable interactions occur between entities during fluid transport.
4. Channel cross-sectional shape and size remains constant over the entire length of the channel (converging or diverging fluid passages in the capture zone are thereby excluded). This implies all fluid travels exclusively in the direction of the channel and there are no variations in velocity along the length.

General Equations (Three Dimensional)

1. Steady-state transport of suspended entities within the channel, due to fluid convection and diffusion effects, where $C=C(x,y,z)$=local entity concentration level:

$$\phi U^*_x \frac{\partial C}{\partial x^*} = \left(\frac{\overline{W}}{L}\right)^2 \frac{\partial^2 C}{\partial x^{*2}} + \frac{\partial^2 C}{\partial y^{*2}} + \frac{\partial^2 C}{\partial z^{*2}} \qquad \phi = \frac{\overline{U}\,\overline{W}^2}{DL}$$

Normalized spatial coordinates and normalized fluid velocity within the channel:

$$x^* = x/L \qquad U^*_x = U_x/\overline{U}$$

$$y^* = y/\overline{W}$$

$$z^* = z/\overline{W}$$

Binding rate equation of entities contacting the channel walls:

$$\left\{ n_y \frac{\partial C}{\partial y^*} + n_z \frac{\partial C}{\partial z^*} = (k\overline{W})C \right\} @ \left\{ \begin{array}{l} y^* = y^*_{wall} + \frac{d}{2\overline{W}} n_y \\ z^* = z^*_{wall} + \frac{d}{2\overline{W}} n_z \end{array} \right\}$$

Flow rate of entities entering the channel and leaving the channel:

$$N_{in} = (\overline{U}\,\overline{W}^2) \oint_{inlet} U^*_x C dy^* dz^* \qquad N_{out} = (\overline{U}\,\overline{W}^2) \oint_{exit} U^*_x C dy^* dz^*$$

Entity capture efficiency value:

$$\epsilon = \frac{N_{in} - N_{out}}{N_{in}} = f\left(\phi, \frac{d}{\overline{W}}, \frac{\overline{W}}{L}, k\overline{W}, U^*_x, C_{inlet}\right)$$

Local density of captured entities along the channel length:

$$\rho(x) = N_{in} \frac{\partial \epsilon}{\partial x} = N_{in} \frac{\partial \epsilon}{\partial \phi} \frac{d\phi}{dx} = -N_{in} \frac{\partial \epsilon}{\partial \phi} \frac{\overline{U}\,\overline{W}^2}{Dx^2}$$

Definition of Symbols

C Local concentration level of suspended entities within the channel=$f(x,y,z)$.

x Spatial coordinate in the channel flow direction (parallel to channel walls).

y, z Spatial coordinates orthogonal to the channel flow direction.

$\overline{W}$ Characteristic channel width value.

L Channel length.

d Entity diameter.

D Entity diffusion coefficient within the fluid.

k Entity binding-reaction coefficient at the channel walls.

$\phi$ Channel dispersion parameter.

$\overline{U}$ Channel average fluid velocity.

$U_x$ Channel fluid velocity profile=$f(y,z)$.

$n_y$ Unit normal vector on the channel wall facing into the fluid (y-component of vector).

$n_z$ Unit normal vector on the channel wall facing into the fluid (z-component of vector).

ε Entity capture efficiency value of the channel.

ρ(x) Local density of captured entities along the channel length (entities/unit length).

$N_{in}$ Total quantity of entities entering the channel.

The device design guidelines for maximizing entity capture by diffusion are; minimizing channel width and flow rates while maximizing capture surface area of the structures. The use of particular structure designs can minimize the fluid dead zones. This allows any immobilized reagent on the surface of the structures to be exposed to the fluid flow.

In addition, the devices of the present invention can have a volumetric fluid flow rate control aspect. In other capillary-driven devices, flow rates show a decrease over time as fluid moves through the device, resulting in a changing capture efficiency over time. The present invention can include a decrease in the capillary dimensions, a change in the cross-sectional area, or a change in wettability to keep total sample flow rate constant over time in the device. The volumetric flow rate control in devices of the present invention allow for a controlled capture efficiency.

Assays utilizing the present invention is described in the following examples. The examples are intended to be embodiments of the present invention and the present invention is not intended to be limited to the examples. In the examples, the structures are arranged in rows across the width of the device. In Examples 2-5, a positive result for analyte in a test sample will produce a visual bar across the width of the device at the capture site.

EXAMPLE 1

The structures are coated with 0.5 microliters (µl) of a 2 milligram per milliliter (mg/ml) solution of anti-beta human thyroid stimulating hormone (hTSH) (Abbott Laboratories, Abbott Park, Ill., 60064) and incubated for 90 minutes at 37° Celsius (C.). The structures are then overcoated with 1 mg/ml bovine serum albumin (BSA) in 3-[N-Morpholino] propanesulfonic acid (MOPS) (Sigma Chemical Co., St. Louis, Mo., 63178) buffer, pH of 7.0, and allowed to incubate for at least 4 hours. The structures are then washed in phosphate buffered saline (PBS) to remove any unbound protein.

The polystyrene structures are top laminated with an adhesive backed Vistex coated polycarbonate film layer.

Samples of 50 µl of hTSH calibrators are introduced into an inlet port of the devices through a 250 µl Hamiliton Syringe (Hamilton Co., Reno, Nev., 89502) driven by a Sage Instruments Syringe Pump (Cole-Parmer Instruments, Chicago, Ill., 60648) at a flow rate of 0.55 µl/minute. The samples are premixed with 282 nanometer (nm) diameter orange fluorescent microparticles in solution (Molecular Probes, Inc., Eugene, Oreg., 97402)with anti-alpha hTSH (Abbott Laboratories) conjugated to the microparticle surface.

The mixture includes 1 part of a 0.1% microparticle solution, 2 parts of IMx® diluent (Abbott Laboratories, Abbott Park, Ill.) and 6 parts of the hTSH calibrators (50 µl=6 parts). The assay is run for approximately 5 minutes.

The devices are analyzed with a reflectance meter using a 2 millimeter (mm) slit beam imaged through a 485 nm excitation filter, a 505 nm dichroic filter, and a 560 nm emission filter. The microparticles have a maximum excitation wavelength of 505 nm and a maximum fluorescence at 560 nm. The parts are scanned across their entire 15 mm length with a sampling rate of 100 points per millimeter. Microparticle capture by structure bound anti-beta hTSH antibody is directly proportional to the hTSH concentration in the sample.

EXAMPLE 2

Black polypyrrole particles are coated with polyclonal goat antibody to hepatitis B surface antigen (anti-HBsAg). The coated polypyrrole particles are applied to the surface of a chamber anterior to the structures of the device. The structures have mouse monoclonal anti-HBsAg antibody immobilized on their surfaces. The mouse monoclonal antibody is reactive to a different surface antigen epitope than the polyclonal goat antibody.

A test sample containing HBsAg is added to the inlet port of the device where it is transported to the chamber. The test sample is mixed with the coated polypyrrole particles whereby test sample HBsAg is specifically bound to the anti-HBsAg coated particles. Capillary action transports the antigen-antibody-particle complex out of the chamber and into the array of structures. The antigen-antibody- particle complex will accumulate at the capture site in proportion to the amount of test sample HBsAg. A visual inspection of the formation of a black bar indicates the presence of HBsAg in the test sample.

EXAMPLE 3

Black polypyrrole particles are coated with a recombinant HBsAg antigen. The coated polypyrrole particles are applied to the surface of a chamber anterior to the structures of the device. The structures are coated with a different recombinant HBsAg antigen. A test sample containing anti-HBsAg antibody is added to the inlet port of the device where it is transported to the chamber. The test sample is mixed with the coated polypyrrole particles whereby test sample anti-HBsAg antibody is specifically bound to the recombinant HBsAg coated particles. Capillary action transports the antibody-antigen-particle complex out of the chamber and into the array of structures. The polypyrrole particles will accumulate at the capture site in proportion to the amount of test sample anti-HBsAg antibody. The presence of the anti-HBsAg antibody in the test sample is determined by the formation of a black bar.

EXAMPLE 4

Black polypyrrole particles are coated with p41 recombinant HIV antigen which is common to both HIV-1 and HIV-2. The coated polypyrrole particles are applied to the surface of a chamber anterior to the structures of the device. The structures are coated with recombinant p41 antigen as well as p24 antigen from both HIV-1 and HIV-2 virus.

A test sample containing anti-HIV antibody is added to the inlet port of the device where it is transported to the chamber. The test sample is mixed with the coated polypyrrole particles whereby test sample anti-HIV antibody specific for the recombinant HIV antigen coated on the particles binds. Capillary action transports the antibody-antigen-particle complex out of the chamber and into the array of structures.

The polypyrrole particles will accumulate at the capture site in proportion to the amount of test sample anti-HIV antibody. A visual inspection of the formation of a black bar indicates the presence of anti-HIV antibody in the test sample.

EXAMPLE 5

Black polypyrrole particles are coated with a mix of monoclonal antibodies specific to HIV antigen common to both HIV-1 and HIV-2. The structures are coated with a mix of monoclonal antibodies specific to HIV antigen common to both HIV-1 and HIV-2 virus.

19

A test sample containing HIV antigen common to both HIV-1 and HIV-2 virus is added to the inlet port of the device where it is transported by capillary action to the array of structures. The HIV antigen common to both HIV-1 and HIV-2 virus in the test sample is specifically bound to the monoclonal antibodies that are coated on the surface of the structures. A solution of coated polypyrrole particles in phosphate buffered saline (PBS) is added to the inlet port and transported by capillary forces to the structures where the polypyrrole particles specifically bind to the HIV antigen captured at the capture site.

The polypyrrole particles will accumulate at the capture site in proportion to the amount of test sample HIV antigen. A visual inspection of the formation of a black bar indicates the presence of HIV antigen in the test sample.

EXAMPLE 6

A polynucleotide is attached to a fluorescent (fluorescein) labelled particle. The coated fluorescent particles are applied to the surface of a chamber anterior to the structures of the device. The structures are also coated with a polynucleotide which is complementary to the nucleotide of interest.

A test sample containing a nucleotide sequence of interest that is present in a test sample or has been amplified via polymerase chain reaction (PCR) or ligase chain reaction (LCR), is added to the inlet port of the device where it is transported to the chamber. The test sample is mixed with the polynucleotide coated fluorescent particles whereby test sample nucleotide of interest binds to the complementary polynucleotide fluorescent labelled particles. Capillary action transports the nucleotide-complementary polynucleotide-fluorescent particle complex out of the chamber and into the array of structures.

The complex will bind at the complementary polynucleotide at the capture site in proportion to the amount of test sample nucleotide of interest.

EXAMPLE 7

A polyanionic material is coupled to a mix of monoclonal anti-HIV antibodies which are specific to HIV antigen common to both HIV-1 and HIV-2. The polyanionic material is placed on the surface of a chamber anterior to the structures of the device. The structures are treated with a cationic solution, such as polyglutamic acid.

A test sample containing HIV antigen common to both HIV-1 and HIV-2 is added to the inlet port of the device where it is transported by capillary action to the chamber. The test sample is mixed with the antibodies coupled to the polyanionic material whereby test sample HIV antigen common to both HIV-1 and HIV-2 will specifically bind to the antibodies. Capillary action transports the HIV antigen-anti-HIV antibody-polyanion complex out of the chamber and into the array of structures.

The polyanionic material will be captured by the cationic material on the surfaces of the structures. Fluorescent (fluorescein) labelled particles coupled to anti-HIV antibodies which are specific to HIV antigen common to both HIV-1 and HIV-2 are added to the inlet port of the device. Capillary action transports the labelled particles coupled to anti-HIV antibodies to the structures of the device where they will bind to HIV antigen common to both HIV-1 and HIV-2 which are captured at the capture site.

The fluorescent labelled particles coupled to anti-HIV antibodies will accumulate at the capture site in proportion to the amount of test sample HIV antigen common to both HIV-1 and HIV-2.

20

We claim:

1. An analytical device for determining the presence or an amount of an analyte in a test sample comprising, in combination:
   a base layer;
   an array of structures arising from said base layer, each of said structures having a surface providing immobilized reagent, said immobilized reagent covalently or non-covalently attached to said surface of said structure, said immobilized reagent capable of binding a member selected from the group consisting of analyte, analyte-analog, ancillary binding member, and labelled reagent; and
   a plurality of channels adjacent to said structures, wherein said test sample containing said analyte, analyte-analog, ancillary binding member, or labelled reagent flows through said channels, said analyte, analyte-analog, ancillary binding member, or labelled reagent diffusing across the width of said channels binding to said immobilized reagent, wherein the ratio of the height of said structures to the average width of said channels is greater than 2:1.

2. The analytical device of claim 1 wherein said analyte and said immobilized reagent comprises an antigen and an antibody.

3. The analytical device of claim 1 wherein said analyte and said immobilized reagent comprises complementary nucleotide sequences.

4. The analytical device of claim 1 wherein said analyte and said immobilized reagent comprises a lectin and a carbohydrate.

5. The analytical device of claim 1 wherein said analyte and said immobilized reagent comprises an avidin and a biotin.

6. The analytical device of claim 1 wherein said structures are made with copolymers, blends, laminates, metallized foils, metallized films or metals deposited on a material selected from the group consisting of:
   polyolefins, polyesters, styrene containing polymers, polycarbonate, acrylic polymers, chlorine containing polymers, acetal homopolymers and copolymers, cellulosics and their esters, cellulose nitrate, fluorine containing polymers, polyamides, polyimides, polyetheretherketone, sulfur containing polymers, polyurethanes, silicon containing polymers, glass, and ceramic materials.

7. The analytical device of claim 1 wherein said structures can have a height ranging from about 1 micrometer to about 1 millimeter.

8. The analytical device of claim 1 wherein said structures can have an average width ranging from about 1 micrometer to about 1 millimeter.

9. The analytical device of claim 1 wherein said channel has a depth ranging from about 1 micrometer to about 1 millimeter.

10. The analytical device of claim 1 wherein said channel has an average width ranging from about 0.02 micrometers to about 20 micrometers.

11. The analytical device of claim 1 wherein said structures in said array of structures are similarly shaped.

12. The analytical device of claim 11 wherein said similarly shaped structures are selected from the group consisting of:
   diamonds, hexagons, octagons, rectangles, squares, circles, semi-circles, triangles and elipses.

13. The analytical device of claim 11 wherein said array of structures are staggered relative to the direction of test sample flow.

14. The analytical device of claim 1 further comprising a labelled reagent, said labelled reagent comprising a detectable label and a specific binding member which is specific for said analyte, analyte-analog, or ancillary binding member.

15. The analytical device of claim 1 wherein a detectable label is added to said analytical device, said detectable label is selected from the group consisting of: non-radioactive isotopes, metal chelators, and direct visual labels.

16. The analytical device of claim 1 wherein said device is a cuvette.

17. The analytical device of claim 1 wherein said device is a dipstick.

18. The analytical device of claim 1 further comprising a separator anterior to said structures.

19. The analytical device of claim 18 wherein said separator is a hydrophilic sintered porous matrix.

20. The analytical device of claim 19 wherein said matrix is treated with a red blood cell agglutinating agent.

21. The analytical device of claim 1 wherein said device has a control means.

22. The analytical device of claim 1 wherein said array of structures have multiple immobilized reagents to test for multiple analytes in said test sample.

23. The analytical device of claim 1 wherein differential pressure is used to drive said test sample through the device.

24. The analytical device of claim 1 wherein chambers are added to said device anterior or posterior to said array of structures.

25. The analytical device of claim 1 wherein said device has at least one alternate pathway.

26. The anaytical device of claim 25 wherein said alternate pathway transports said test sample to a separate array of structures.

27. The analytical device of claim 1 wherein said ancillary binding member binds to said analyte, and said analyte binds to said immobilized reagent.

28. The analytical device of claim 1 wherein said structures and channels of said devices are manufactured by at least one of the following steps: lasering, micromachining, photolithography, reactive ion etching, ion beam milling, embossing, electroforming, electroplating, injection molding, compression molding, casting, or reaction injection molding.

29. The analytical device of claim 28 wherein said direct visual labels are selected from the group consisting of fluorescent signals, chemiluminescent signals, and enzymatic signals.

30. An analytical device for determining the presence or an amount of an analyte in a test sample comprising, in combination:

a base layer;

an inlet port and a vent;

an array of structures arising from said base layer, each of said structures having a surface providing a capture site for said analyte;

an immobilized reagent, said immobilized reagent covalently or non-covalently attached to said surface of said structure, said immobilized reagent capable of binding an a member selected from the group comprising: analyte, analyte-analog, and an ancillary binding member;

a plurality of channels adjacent to said structures, wherein said test sample containing said analyte, analyte-analog, or ancillary binding member flows through said channels, said analyte, analyte-analog, or ancillary binding member diffusing across the width of said channels to bind said immobilized reagent; and a labelled reagent comprising a specific binding member conjugated to a detectable label, said detectable label capable of producing a signal at said capture site, said signal indicating the presence or amount of said analyte present in said test sample, wherein the ratio of the height of said structures to the average width of said channels is greater than 2:1.

* * * * *